US011744809B2

(12) United States Patent
Stroppolo et al.

(10) Patent No.: US 11,744,809 B2
(45) Date of Patent: Sep. 5, 2023

(54) EXTENDED RELEASE TABLET COMPRISING A WEIGHT-LOSS DRUG

(71) Applicant: ALPEX PHARMA SA, Mezzovico (CH)

(72) Inventors: Federico Stroppolo, Aldesago (CH); Gabriele Granata, Leggiuno (IT)

(73) Assignee: ALPEX PHARMA SA, Mezzovico (CH)

( * ) Notice: Subject to any disclaimer, the term of this patent is extended or adjusted under 35 U.S.C. 154(b) by 27 days.

(21) Appl. No.: 16/343,914

(22) PCT Filed: Nov. 7, 2017

(86) PCT No.: PCT/EP2017/078500
§ 371 (c)(1),
(2) Date: Apr. 22, 2019

(87) PCT Pub. No.: WO2018/087097
PCT Pub. Date: May 17, 2018

(65) Prior Publication Data
US 2019/0254993 A1    Aug. 22, 2019

(30) Foreign Application Priority Data

Nov. 8, 2016   (EP) .................................... 16197747

(51) Int. Cl.
| | |
|---|---|
| *A61K 31/137* | (2006.01) |
| *A61K 47/36* | (2006.01) |
| *A61K 47/26* | (2006.01) |
| *A61K 47/10* | (2017.01) |
| *A61K 47/12* | (2006.01) |
| *A61K 9/20* | (2006.01) |
| *A61P 3/04* | (2006.01) |

(52) U.S. Cl.
CPC .......... *A61K 31/137* (2013.01); *A61K 9/2013* (2013.01); *A61K 9/2018* (2013.01); *A61K 9/2059* (2013.01); *A61K 47/10* (2013.01); *A61K 47/12* (2013.01); *A61K 47/26* (2013.01); *A61K 47/36* (2013.01); *A61P 3/04* (2018.01)

(58) Field of Classification Search
CPC ...... A61K 31/137; A61K 47/10; A61K 47/12; A61K 47/36; A61K 47/26
See application file for complete search history.

(56) References Cited

U.S. PATENT DOCUMENTS

| | | | |
|---|---|---|---|
| 9,125,833 | B2 * | 9/2015 | Babul ..................... A61P 25/04 |
| 2008/0206327 | A1 | 8/2008 | Stroppolo et al. |

FOREIGN PATENT DOCUMENTS

| WO | 2006104397 A1 | 10/2006 |
|---|---|---|
| WO | 2011035343 A2 | 3/2011 |
| WO | 2018087097 A1 | 5/2018 |

OTHER PUBLICATIONS

Quadir et al.; "Evaluation of Hydrophobic Materials as Matrices for Controlled-Release Drug Delivery"; 2003; Pakistan Journal of Pharmaceutical Sciences; 16(2): 17-28 (Year: 2003).*
"Phentermine Resin ER—phentermine capsule, extended release", Lannett Company, Inc., 2011, XP-002766213, retrieved from URL:https://dailymed.nlm.nih.gov/dailymed/ archives/fdaDruginfo. cfm?archiveid=61002., pp. 1-14.
Kang et al., "Randomized controlled trial to investigate the effects of a newly developed formulation of phentermine diffuse-controlled release for obesity", Diabetes, Obesity and Metabolism, 2010, vol. 12, No. 10, pp. 876-882.
International Search Report and Written Opinion for Corresponding International Application No. PCT/EP2017/078500 (13 Pages) (dated Mar. 7, 2018).
"A 12-Week Randomized, Double-Blind, Placebo-Controlled Phase 3 Trial of the Efficacy and Safety of Appetite Suppressant, New Formulation of Pentermine 30mg Diffuse Controlled Release in the Treatment of Korean Obese Patients", American Diabetes Association, 2009, 2 pages.
Momoh et al., "Formulation and evaluation of novel solid lipid microparticles as a sustained release system for the delivery of metformin hydrochloride", Drug Deliv, 2013, vol. 20, No. 3-4, pp. 102-111.
Quadir et al., "Evaluation of Hydrophobic Materials as Matrices for Controlled-Release Drug Delivery", Pakistan Journal of Pharmaceutical Sciences, 2003, vol. 16, No. 2, pp. 17-28.
Nisha et al., "Matrix Tablets: An Effective Way for Oral Controlled Release Drug Delivery", Iranian Journal of Pharmaceutical Sciences, 2012, vol. 8, No. 3, pp. 165-170.
Shanmugam et al., "Formulation and Evaluation of Sustained Release Matrix Tablets of Venlafaxine Hydrochloride", BioMedRx, 2013, vol. 1, No. 5, pp. 506-510.
Yadav et al., "Evaluation of hydrophilic, hydrophobic and waxy matrix excipients for sustained release tablets of Venlafaxine hydrochloride", Drug Development and Industrial Pharmacy, 2012, pp. 1-10.
Almeida et al., "Comparative study of sustained-release lipid microparticles and solid dispersions containing ibuprofen", Brazilian Journal of Pharmaceutical Sciences, 2012, vol. 48, No. 3, pp. 529-536.
Rowe et al., "Handbook of Pharmaceutical Excipients", Pharmaceutical Press, Sixth Edition, pp. 1-917.
"Maltodextrin", Handbook of Pharmaceutical Excipients, pp. 317-319.
Sievert et al., "Dissolution Tests for ER Products", Workshop for The Role of the Biopharmaceutical Classification System and In Vitro—In Vivo Correlations in the Approval of Oral Drug Product, 1998, pp. 1-15.

* cited by examiner

*Primary Examiner* — Timothy P Thomas
(74) *Attorney, Agent, or Firm* — Lucas & Mercanti, LLP

(57) ABSTRACT

An extended release tablet (ERT), having phentermine or a pharmaceutically acceptable salt thereof, and one or more of a wax and a pharmaceutically acceptable excipient selected from among one or more of a fatty acid, a bulking agent, a lubricant and the like is disclosed. A process for its preparation is also disclosed.

6 Claims, No Drawings

EXTENDED RELEASE TABLET COMPRISING A WEIGHT-LOSS DRUG

CROSS-REFERENCE TO RELATED APPLICATIONS

This application is a 371 of PCT/EP2017/078500, filed Nov. 7, 2017, which claims the benefit of European Patent Application No. 16197747.5, filed Nov. 8, 2016.

FIELD OF THE INVENTION

The present invention relates to an extended release tablet (ERT), comprising phentermine or a pharmaceutically acceptable salt thereof and one or more of a wax and at least a pharmaceutically acceptable excipient selected among one or more of a fatty acid, a bulking agent, a lubricant and the like and a process for its preparation.

BACKGROUND OF THE INVENTION

The prevalence of overweight people has reached alarming levels. Also the proportion of children and adolescents who are overweight has tripled in the past three decades.

Obesity arises as a consequence of positive caloric balance. A comprehensive behavioral approach comprising a gradual increase of energy expenditure from exercise and an appropriate diet to decrease the caloric intake should be the more effective treatment of obesity.

However, this approach has a relatively low success rate. Consequently alternative forms of treatment, including surgery and/or medication, have been developed in an effort to increase the likelihood of achieving, and maintaining weight loss. In particular pharmacotherapy, in combination with intensive behavioral treatment, can lead to clinically significant decreases in body weight in obese population.

Some US FDA-approved weight-loss drugs are phentermine, sibutramine, orlistat, diethylpropion, and lorcaserin. Liraglutide has been also approved for the treatment of overweight. Among them, phentermine is more commonly used since it is one of the most efficient and safe in promoting weight loss or in maintaining a healthy body weight, especially when given along with recommendations for diet and exercise.

Phentermine is a sympathomimetic amine which first received approval from the US FDA in 1959 as an appetite suppressant for the short-term treatment of exogenous obesity for patients with an initial body mass index $\geq 30$ kg/m$^2$, or $\geq 27$ kg/m$^2$ in the presence of other risk factors (e.g., hypertension, diabetes, and hyperlipidemia). Phentermine hydrochloride ($\alpha,\alpha$-dimethylphenethylamine hydrochloride) became available in the United States in the early seventies and is currently sold in several dosage forms such as tablets, film coated tablets and capsules.

WO 2006/104397 discloses a controlled release combination tablet comprising a copper antagonist, such as copper chelators, and one or more anorectics, such as phentermine maleate, prepared by roller compaction and direct compression methods. However, in such dosage form, nearly 70% of the total weight is occupied by the copper antagonist leaving a very small formulation space for the anorectic and other suitable excipients. Furthermore, the manufacturing process employed is not the best suited when lipid excipients are involved.

Extended release formulations in the form of capsules containing phentermine in order to suppress appetite during all the day are marketed in some countries such as Australia, New Zealand and South Africa under the trade name Duromine®. Duromine® composition is in the form of granules contained in a hard gelatine capsule.

Duromine® contains an ion exchange resin which reacts with phentermine base under specific conditions.

The ion-exchange resin contained in Duromine® is quite stable, highly insoluble and without pharmacological effect until it reacts with cations (hydrogen, potassium, sodium etc.) present in the gastrointestinal fluids.

In particular, the resin contained in Duromine®, after administration and in the presence of the ions of the gastrointestinal tract exchanges sodium ions with phentermine providing the release of the active ingredient.

However, the extended release capsules containing phentermine known in the art, such as Duromine®, have several disadvantages.

In fact, the reaction between the ion exchange resin present in Duromine® and phentermine is influenced by the ionic strength in gastrointestinal fluids. Therefore, the release and dissolution of phentermine from Duromine® may be different in the same patient at different times and from patient to patient. This variability highly impacts on the bioavailability and efficacy of the drug.

Moreover, since Duromine® is in the form of hard gelatine capsules, said capsules cannot be divided, therefore they are not suitable for dose adjustments.

The marketed tablets containing phentermine are manufactured so as to release phentermine immediately or in short terms.

However, there is the need of an effective extended release formulation comprising phentermine or a pharmaceutically acceptable salt thereof which ensures a constant and reproducible release and dissolution of phentermine or a salt thereof and which can be administered even only once a day.

The present invention provides an extended release tablet which solves the drawbacks or disadvantages of the extended release formulations comprising weight-loss drugs, in particular phentermine or a salt thereof, known in the art.

Such extended release tablet comprising phentermine or a pharmaceutically acceptable salt thereof is suitable for administration for longer terms, ensures the constant and reproducible release and dissolution of phentermine and its optimal efficacy and minimizes the difference or variability of efficacy of the drug among patients.

SUMMARY OF THE INVENTION

In one aspect, the present invention relates to an extended release tablet comprising phentermine or a pharmaceutically acceptable salt thereof for weight control in humans, especially in children and adolescents, and one or more of a wax and at least one pharmaceutically acceptable excipient selected among one or more of a fatty acid, a bulking agent, a lubricant and the like.

In a further preferred embodiment, the present invention relates to an extended release tablet comprising phentermine hydrochloride and one or more of a wax and at least one pharmaceutically acceptable excipient selected among one or more of a fatty acid, a bulking agent, a lubricant and the like.

In a further aspect, the present invention relates to an extended release tablet able to release in vitro and in vivo phentermine or a pharmaceutically acceptable salt thereof, for over seven hours.

DETAILED DESCRIPTION OF EMBODIMENTS OF THE INVENTION

A first object of the present invention is an extended release tablet (ERT) comprising phentermine or a pharmaceutically acceptable salt thereof and one or more of a wax and at least a pharmaceutically acceptable excipient selected among one or more of a fatty acid, a bulking agent, a lubricant and the like.

A preferred extended release tablet according to the present invention comprises phentermine hydrochloride.

Typically, a wax used in the extended release tablet of the present invention is selected among cetostearyl alcohol, carnauba wax, beeswax, candelilla wax, soy wax, palm wax, paraffin wax, and microcrystalline wax and mixtures thereof. Preferably, the wax is cetostearyl alcohol.

The fatty acid used in the extended release tablet of the present invention is selected among stearic acid and salts thereof, palmitic acid and stearin, preferably the fatty acid is stearic acid.

A bulking agent according to the present invention can be a polyalcohol, a dextrin or mixtures thereof.

The polyalcohol is typically selected among glycerol, erythritol, threitol, arabitol, ribitol, mannitol, sorbitol, galactitol, fucitol, iditol, inositol, volemitol, isomalt, xylitol, lactitol, maltitol or mixtures thereof. Preferably the polyalcohol is sorbitol.

The dextrin is typically selected among maltodextrin, amylodextrins, erythrodextrins, achrodextrins, cyclodextrins. Preferably the dextrin is maltodextrin.

The lubricant according to the present invention is typically selected among sodium stearate, calcium stearate, magnesium stearate, magnesium trisilicate, sodium stearyl fumarate, stearic acid, potassium stearate, zinc stearate, hydrogenated ricin oil and mixtures thereof. Preferably the lubricant is magnesium stearate, stearic acid or hydrogenated ricin oil, more preferably magnesium stearate.

According to a preferred embodiment, in the present extended release tablet phentermine or a pharmaceutically acceptable salt thereof is present in an amount from about 1% to about 15% of the total weight of the tablet. In addition, the bulking agent is in an amount from about 60% to about 90% of the total weight of the tablet, preferably from about 65% to about 82% of the total weight of the tablet.

Moreover, the wax, the fatty acid and the lubricant in the tablet of the present invention are in an overall amount from about 9% to about 39% of the total weight of the tablet, preferably from about 15% to about 30% of the total weight of the tablet.

Preferably, the lubricant present in the extended release tablet according to the present invention is in a weight amount from about 0.1% to about 3% of the total weight of the tablet, more preferably from about 0.5% to about 1.5% of the total weight of the tablet.

According to the present invention a dextrin, a polyalcohol or mixtures thereof are defined as hydrophilic excipients while a wax, a fatty acid and a lubricant are defined as hydrophobic excipients.

According to a preferred embodiment, the weight ratio between hydrophilic excipients (dextrin, polyalcohol or mixtures thereof) and hydrophobic excipients (wax, fatty acid and lubricant) is between 3 and 3.5.

Preferably the weight ratio dextrin/polyalcohol is between 0.5 and 1.5.

Preferably the weight ratio wax/fatty acid and lubricant is between 0.5 and 1.5.

Moreover, the weight ratio fatty acid/lubricant is typically from 15:1 to 8:1, preferably about 10:1.

According to a preferred embodiment, an extended release tablet according to the present invention comprises phentermine hydrochloride, cetostearyl alcohol, stearic acid, sorbitol, maltodextrin and magnesium stearate.

Unless otherwise specified, when referring to "phentermine", "phentermine or a pharmaceutically acceptable salt thereof" or "phentermine hydrochloride", the given dosage is expressed as the weight of the free base.

Preferably, the extended release tablet of the present invention comprises phentermine or a pharmaceutically acceptable salt thereof in an amount from 2.5 mg to 40 mg, more preferably from 15 mg to 40 mg, per dosage form.

In a preferred embodiment, the extended release tablet of the present invention comprises phentermine hydrochloride in an amount from 2.5 mg to 40 mg per dosage form, more preferably in an amount from 15 mg to 40 mg per dosage form. Even more preferably, the extended release tablet of the present invention comprises phentermine hydrochloride in an amount of 15 mg, 30 mg, or 40 mg per dosage form.

The extended release tablet according to the present invention can also comprise a sweetener selected among aspartame, saccharin, sucralose or a *Stevia rebaudiana* derivative or mixtures thereof.

The extended release tablet according to the present invention can also comprise a flavoring agent, typically a synthetic or natural flavor, such as cinnamon, peppermint, clove, anise, *eucalyptus*, thyme, cedar, chamomile oils, fruit essences such as apple, peach, strawberry, raspberry, orange, apricot, cherry, plum, pineapple, or mixtures thereof.

A particularly preferred embodiment of the present invention is an extended release tablet comprising:

| | |
|---|---|
| Phentermine or a salt thereof | 1-15% w/w |
| A dextrin and a polyalcohol | 60-90% w/w |
| A wax, a fatty acid and a lubricant | 9-39% w/w |
| The total weight being | 100% |
| Preferably the extended release tablet comprises: | |
| Phentermine or a salt thereof | 1.5-8% w/w |
| A dextrin and a polyalcohol | 65-82% w/w |
| A wax, a fatty acid and a lubricant | 15-30% w/w |
| The total weight being | 100% | wherein the weight ratio between dextrin/polyalcohol is between 0.5 and 1.5, the weight ratio wax/fatty acid and lubricant is between 0.5 and 1.5 and the weight ratio fatty acid/lubricant is from 15:1 to 8:1, preferably about 10:1.

More preferably, the extended release tablet of the present invention comprises

| | |
|---|---|
| Phentermine hydrochloride | 1.5-8% w/w |
| Maltodextrin and sorbitol | 65-82% w/w |
| Cetostearyl alcohol, stearic acid and magnesium stearate | 15-30% w/w |
| The total weight being | 100% | wherein the weight ratio between dextrin/polyalcohol is between 0.5 and 1.5, the weight ratio wax/fatty acid and lubricant is between 0.5 and 1.5 and the weight ratio fatty acid/lubricant is from 15:1 to 8:1, preferably about 10:1.

Preferably the extended release tablet comprises:

| | |
|---|---|
| Phentermine or a salt thereof | 3-8% w/w |
| A dextrin and a polyalcohol | 65-82% w/w |
| A wax, a fatty acid and a lubricant | 15-30% w/w |
| The total weight being | 100% | wherein the weight ratio between dextrin/polyalcohol is between 0.5 and 1.5, the weight ratio wax/fatty acid and lubricant is between 0.5 and 1.5 and the weight ratio fatty acid/lubricant is from 15:1 to 8:1, preferably about 10:1.

More preferably, the extended release tablet of the present invention comprises

| | |
|---|---|
| Phentermine hydrochloride | 3-8% w/w |
| Maltodextrin and sorbitol | 65-82% w/w |
| Cetostearyl alcohol, stearic acid and magnesium stearate | 15-30% w/w |
| The total weight being | 100% | wherein the weight ratio between dextrin/polyalcohol is between 0.5 and 1.5, the weight ratio wax/fatty acid and lubricant is between 0.5 and 1.5 and the weight ratio fatty acid/lubricant is from 15:1 to 8:1, preferably about 10:1.

In particular, the extended release tablet of the present invention may have one of the following compositions:

| | | |
|---|---|---|
| Phentermine HCl | 18.65 mg | (equivalent to 15 mg phentermine free base) |
| Maltodextrin | 108.00 mg | |
| Sorbitol | 107.85 mg | |
| Cetostearyl Alcohol | 31.25 mg | |
| Stearic Acid | 31.25 mg | |
| Magnesium Stearate | 3.0 mg | |
| TOTAL WEIGHT | 300.0 mg | |
| or | | |
| Phentermine HCl | 18.65 mg | (equivalent to 15 mg phentermine free base) |
| Maltodextrin | 287.75 mg | |
| Sorbitol | 288.00 mg | |
| Cetostearyl Alcohol | 83.30 mg | |
| Stearic Acid | 83.30 mg | |
| Magnesium Stearate | 8.0 mg | |
| TOTAL WEIGHT | 769.0 mg | |
| or | | |
| Phentermine HCl | 37.3 mg | (equivalent to 30 mg phentermine free base) |
| Maltodextrin | 216 mg | |
| Sorbitol | 215.7 mg | |
| Cetostearyl Alcohol | 62.5 mg | |
| Stearic Acid | 62.5 mg | |
| Magnesium Stearate | 6.0 mg | |
| TOTAL WEIGHT | 600.0 mg | |
| or | | |
| Phentermine HCl | 37.3 mg | (equivalent to 30 mg phentermine free base) |
| Maltodextrin | 287.70 mg | |
| Sorbitol | 288 mg | |
| Cetostearyl Alcohol | 83.30 mg | |
| Stearic Acid | 83.30 mg | |
| Magnesium Stearate | 8.0 mg | |
| TOTAL WEIGHT | 787.6 mg | |
| or | | |
| Phentermine HCl | 49.74 mg | (equivalent to 40 mg phentermine free base) |
| Maltodextrin | 288 mg | |
| Sorbitol | 287.6 mg | |
| Cetostearyl Alcohol | 83.33 mg | |
| Stearic Acid | 83.33 mg | |
| Magnesium Stearate | 8.0 mg | |
| TOTAL WEIGHT | 800.0 mg | |

The extended release tablet according to the present invention can also be coated, colored, scored and/or embossed in order to comply with regulatory requirements and for patient compliance.

In particular, the tablet can be coated with a colored film for an easier identification. Therefore, the extended release tablet according to the present invention can optionally comprise one or more pharmaceutically acceptable coloring agents, preferably from about 0.01% to about 0.5% of the total weight of the tablet.

According to a preferred embodiment, the extended release tablet of the present invention is scored and colored in green, red brown or orange.

More preferably, the extended release tablet according to the present invention has a capsule shape, is scored and colored and can be divided following a breaking line in two halves and is embossed with an identification code.

If the case, the extended release tablets of the present invention can be packed in PVC/PVDC or in ALU/ALU blister packs, wherein each blister comprises 10 tablets.

If the case, the extended release tablets of the present invention can also be packed in a bottle, for example a High Density Polyethylene (HDPE) bottle, equipped with a child resistant closure (CRC) and/or a tamper-evident seal.

The extended release tablet according to the present invention can be manufactured according to techniques known in the art.

In particular, the extended release tablet according to the present invention can be manufactured according to a melting technology, such as sieving, melting granulation, blending and tableting.

In a preferred embodiment, the manufacturing process of the extended release tablet according to the present invention is disclosed here below.

The process comprises the steps of:
a) granulating a mixture comprising phentermine or a salt thereof, a bulking agent, a fatty acid and a wax, without using water or other solvents, rising the temperature between about 35° C. and about 65° C.;
b) compressing the homogenous mixture into a tablet.

A salt of phentermine is a pharmaceutically acceptable one, preferably the hydrochloride salt.

The bulking agent, fatty acid and wax are as defined above.

"Without using any solvent" means that the process does not make use of any organic or inorganic solvent.

Optionally, before granulating the mixture at step a), the active ingredient and the excipients can be loaded in a high shear mixer.

Optionally, after the granulation step a) the granulate can be sieved, in particular through a net of 1 mm net light, and blended with a lubricant, as previously defined, in a bin blender.

The tablets obtained at step b) typically have a content of phentermine or a pharmaceutically acceptable salt thereof corresponding to 15 mg, 30 mg or 40 mg per tablet.

The process of the present invention allows to obtain tablets, in particular extended release tablets, having a homogeneous distribution of phentermine or salt thereof.

It should be noticed that the inventors of the present extended release tablet have advantageously and surprisingly found that the release and dissolution of phentermine or a salt thereof contained in the present tablet is constant and reproducible and it is not influenced by the pH at all. In Example 5 reported here below it is shown that the extended release tablet of the present invention is able to release phentermine or a pharmaceutically acceptable salt thereof, in vitro or in vivo, independently from the pH of the dissolution medium.

Therefore, the release of phentermine or a pharmaceutically acceptable salt thereof from the present extended release tablet can be defined as pH independent and ionic strength independent.

Furthermore, the duration of the release of phentermine or a pharmaceutically acceptable salt thereof contained in the extended release tablet of the present invention is greater than seven hours.

In conclusion, the extended release tablet of the present invention ensures the optimal efficacy of phentermine or a pharmaceutically acceptable salt thereof and minimizes the variability of absorption of the active ingredient among patients so achieving a regular and reproducible bioavailability profile, compared to the extended release formulations containing phentermine or a pharmaceutically acceptable salt thereof known in the art.

Moreover, the extended release tablet according to the present invention is stable, easy to be administered because it requires just to be swallowed with some water.

It is therefore another object of the present invention an extended release tablet, as disclosed above, which releases phentermine or a pharmaceutically acceptable salt thereof independently from the pH of the dissolution medium.

The advantageous properties of the extended release tablet of the present invention make it particularly in compliance with the need of the overweight patients, especially children and adolescents, because it can be administered once a day avoiding repeated administration.

It is therefore another object of the present invention an extended release tablet as disclosed above for use in the treatment of obesity or overweight in humans, preferably in children or adolescents.

Even if the present invention has been disclosed with reference to a specific pharmaceutical formulation comprising phentermine or a salt thereof, the man skilled in the art can also adapt the specific pharmaceutical formulation comprising phentermine or a salt thereof of the present invention to analogous weight-loss drugs. Therefore, an analogous pharmaceutical composition of the present invention, only differing for the kind of weight-loss drug, is to be considered within the scope of the present invention.

The following examples better illustrate the present invention without limiting it.

Example 1

Preparation of an extended release tablet comprising phentermine hydrochloride. Phentermine hydrochloride (supplied by Siegfried, N.J.-US), maltodextrin (supplied by Cargill), sorbitol (supplied by Roquette), cetostearyl alcohol (supplied by BTC Europe), and stearic acid (supplied by Stearinerie Dubois), were sieved and loaded in high share mixer granulator model Henschel-Krupp. Magnesium stearate (supplied by Faci-Genoa, Italy) were added to the external phase and the mixture was blended for 10 minutes at 20 rpm with cube mixer. The blended mixture were then compressed by Ronchi AR90 18 punches tabletting machine, in capsule shaped scored tablets, having the following composition:

| | | |
|---|---|---|
| Phentermine HCl | 18.65 mg | (equivalent to 15 mg of phentermine free base) |
| Maltodextrin | 108.00 mg | |
| Sorbitol | 107.85 mg | |
| Cetostearyl Alcohol | 31.25 mg | |
| Stearic Acid | 31.25 mg | |
| Magnesium Stearate | 3.0 mg | |
| TOTAL WEIGHT | 300.0 mg | |

The tablets can be coated in green with an Opadry film supplied by Colorcon UK.

The tablets are then packed in a blister pack made with PVC/PVDC polymer and back foil in aluminum.

Example 2

Following the procedure described in example 1, extended release tablets as capsule shape scored tablets, having the following composition were prepared:

| | | |
|---|---|---|
| Phentermine HCl | 37.3 mg | (equivalent to 30 mg of phentermine free base) |
| Maltodextrin | 216 mg | |
| Sorbitol | 215.7 mg | |
| Cetostearyl Alcohol | 62.5 mg | |
| Stearic Acid | 62.5 mg | |
| Magnesium Stearate | 6.0 mg | |
| TOTAL WEIGHT | 600.0 mg | |

The tablets can be coated in red-brown with an Opadry film supplied by Colorcon UK.

The tablets are then packed in a blister pack made with PVC/PVDC polymer and back foil in aluminum.

Example 3

Following the procedure described in example 1, extended release tablets, as capsule shape scored tablets having the following composition were prepared:

| | | |
|---|---|---|
| Phentermine HCl | 49.74 mg | (equivalent to 40 mg of phentermine free base) |
| Maltodextrin | 288 mg | |
| Sorbitol | 287.6 mg | |
| Cetostearyl Alcohol | 83.33 mg | |
| Stearic Acid | 83.33 mg | |
| Magnesium Stearate | 8.0 mg | |
| TOTAL WEIGHT | 800.0 mg | |

The tablets can be coated in orange color with an Opadry film supplied by Colorcon U K.

The tablets are then packed in a blister pack made with PVC/PVDC polymer and back foil in aluminum.

Example 4

Determination of the physico-chemical characteristics of extended release tablets comprising phentermine hydrochloride.

Extended release tablets comprising phentermine hydrochloride in different strengths, prepared according to the procedure described in example 1, were analysed and the analytical results are reported hereinafter.

| Dosage strength (mg/tablet) 40 mg | |
|---|---|
| Average Weight | 820 mg |
| Hardness | 11 Kp |

| Dosage strength (mg/tablet) 40 mg | |
|---|---|
| Thickness | 7.6 mm |
| Length | 18.0 mm |
| Width | 7.6 mm |
| Dissolution | 1 hour 25-45% |
| | 3.5 hours 55-75% |
| | 7 hours >70% |
| Phentermine Identification | HPLC: Positive |
| | UV: Positive |
| Phentermine Assay | 95.0-105.0% of the claim |
| | (38.0-42.0 mg/tbl) |
| Content Uniformity | Complies |
| Related Substances & Impurities | 1-Phenylisobutylamine HCl NMT 0.15% |
| | N-(1,1-dimethyl-2-phenylethyl)formamide NMT 0.15% |
| | 3,4-Dihydro-3,3-dimethylisoquinoline NMT 0.15% |
| | Any individual unknown impurity NMT 0.10% |
| | Total impurities NMT 0.30% |
| Microbial Contamination | Total aerobic microbial count <103 UFC/g |
| | Molds & Yeasts count <102 UFC/g |
| | E. coli absent/g |

| Dosage strength (mg/tablet) 30 mg | |
|---|---|
| Average Weight | 620 mg |
| Hardness | 8-14 Kp |
| Thickness | 7.2 mm |
| Length | 18.0 mm |
| Width | 7.6 mm |
| Dissolution | 1 hour 25-45% |
| | 3.5 hours 55-75% |
| | 7 hours >70% |
| Phentermine Identification | HPLC: Positive |
| | UV: Positive |
| Phentermine Assay | 95.0-105.0% of the claim |
| | (28.5-31.5 mg/tbl) |
| Content Uniformity | Complies |
| Related Substances & Impurities | 1-Phenylisobutylamine HCl NMT 0.15% |
| | N-(1,1-dimethyl-2-phenylethyl)formamide NMT 0.15% |
| | 3,4-Dihydro-3,3-dimethylisoquinoline NMT 0.15% |
| | Any individual unknown impurity NMT 0.10% |
| | Total impurities NMT 0.30% |
| Microbial Contamination | Total aerobic microbial count <103 UFC/g |
| | Molds & Yeasts count <102 UFC/g |
| | E. coli absent/g |

| Dosage strength (mg/tablet) 15 mg | |
|---|---|
| Average Weight | 320 mg |
| Hardness | 8-14 Kp |
| Thickness | 4.5 mm |
| Length | 15.0 mm |
| Width | 5.0 mm |
| Dissolution | 1 hour 25-45% |
| | 3.5 hours 55-75% |
| | 7 hours >70% |
| Phentermine Identification | HPLC: Positive |
| | UV: Positive |
| Phentermine Assay | 95.0-105.0% of the claim |
| | (14.25-15.75 mg/tbl) |
| Content Uniformity | Complies |
| Related Substances & Impurities | 1-Phenylisobutylamine HCl NMT 0.15% |
| | N-(1,1-dimethyl-2-phenylethyl)formamide NMT 0.15% |
| | 3,4-Dihydro-3,3-dimethylisoquinoline NMT 0.15% |
| | Any individual unknown impurity NMT 0.10% |
| | Total impurities NMT 0.30% |
| Microbial Contamination | Total aerobic microbial count <103 UFC/g |
| | Molds & Yeasts count <102 UFC/g |
| | E. coli absent/g |

Example 5

Dissolution profile of phentermine hydrochloride prepared according to Example 3 at different media is reported here below.

In the table the substantial independence of the dissolution profile of phentermine independently from the pH is reported

| Time | pH 1.2 | pH 4.5 | pH 6.8 |
|---|---|---|---|
| 1 hour | 40% | 30% | 32% |
| 3.5 hours | 72% | 54% | 60% |
| 7 hours | 93% | 73% | 80% |

The invention claimed is:

1. An extended release tablet consisting of
   a) 1-15% wt. Phentermine HCl;
   b) 15-30% wt. hydrophobic excipients consisting of cetostearyl alcohol, stearic acid, and magnesium stearate; and
   c) 65-82% wt. hydrophilic excipients consisting of a mixture of maltodextrin and sorbitol;
   wherein: i) the ratio of the hydrophilic excipients to the hydrophobic excipients is from 3 to 3.5:1; and ii) the ratio of the maltodextrin to sorbitol in the hydrophilic excipient mixture is 1:1.

2. The extended release tablet of claim 1, wherein the magnesium stearate is present in an amount of from 0.1% to 3% wt. of the extended release tablet.

3. The extended release tablet of claim 1, wherein the weight ratio of the cetostearyl alcohol to stearic acid is from 0.5 to 1.5 to 1.

4. The extended release tablet of claim 1, wherein the weight ratio for the stearic acid to magnesium stearate is from 15:1 to 8:1.

5. The extended release tablet of claim 1, wherein the amount of phentermine HCl is from 1.5-8% wt.

6. The extended release tablet of claim 5, wherein the amount of phentermine HCl is from 3-8% wt.

\* \* \* \* \*